United States Patent [19]

Logothetis

[11] Patent Number: 4,521,237
[45] Date of Patent: Jun. 4, 1985

[54] GLASS DOSE SYRINGE

[75] Inventor: Emanuel N. Logothetis, Short Hills, N.J.

[73] Assignee: Kahle Engineering Co., Union City, N.J.

[21] Appl. No.: 496,929

[22] Filed: May 23, 1983

[51] Int. Cl.³ .................. C03B 29/00; A61M 5/32
[52] U.S. Cl. .................... 65/42; 65/59.25; 65/59.31; 65/59.35; 604/240
[58] Field of Search .......... 65/59.25, 59.31, 59.35, 65/59.27, 59.6, 36, 42; 604/240

[56] References Cited

U.S. PATENT DOCUMENTS

Re. 28,713  2/1976  Stevens et al. ............ 604/240
3,364,002   1/1968  Michel ..................... 65/59.2

FOREIGN PATENT DOCUMENTS 124964  7/1947  Australia ................... 604/240
165310  1/1954  Australia ................... 604/240
918060  2/1963  United Kingdom ............ 604/240

Primary Examiner—Robert Lindsay
Attorney, Agent, or Firm—Stoll, Wilkie, Previto & Hoffman

[57] ABSTRACT

A disposable, single-use, medication charged syringe is described wherein the syringe body is formed with a tubular glass barrel having a steel needle mounted on the barrel by means of a tubular glass bead. The beading and barrel are initially made from common stock of right circular hollow cylindrical tubes. The syringe body is formed by a number of steps including a barrel flaring operation and a needle attaching operation in which the needle is first sealed to the glass tubular bead before the glass bead is sealed to the glass barrel. Identification of the syringe and the particular unit dose therein is provided by a flared colored plastic gripping sleeve which is slipped over the glass barrel.

11 Claims, 7 Drawing Figures

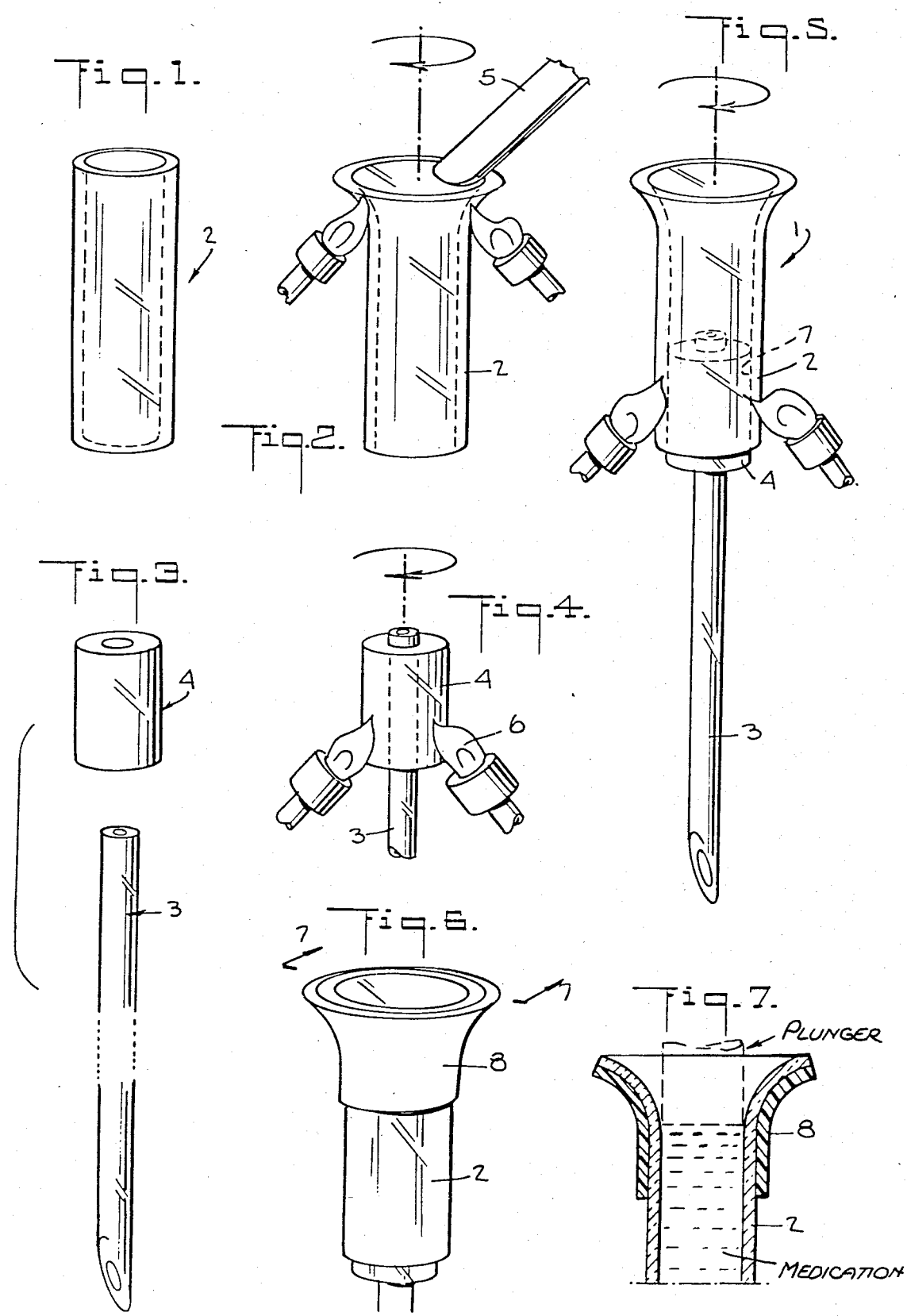

GLASS DOSE SYRINGE

BACKGROUND OF THE INVENTION

The present invention relates to an improved disposable glass syringe and to its method of manufacture. More particularly, a disposable, single use, one charge, glass syringe is provided which is easily manufactured by automatic machinery using a minimum number of steps. A glass, one charge dose, disposable syringe is provided which is useful for a variety of dosage sizes including relatively small dosages and the medicine may be stored in-situ in the disposable syringe for long periods without any contamination from the syringe itself.

The everyday practice of medicine necessitates the use of a syringe for injectable medicines. However, the cost of the syringe due to the common methods of manufacture prohibit its disposal, and it must be cleaned each time after use to prevent contamination from patient to patient.

Disposable syringes are in use today but they are universally made of plastics. This necessitates the current system of transferring medicine from a vial container to the syringe just prior to use. This also necessitates discarding that portion of the vial which is inadequate for a full dose because of batch control limitations in hospitals. Both of these factors contribute to cost of injectable medications.

It has been found that logistic controls such as inventory, data monitoring, transfer handling, and contamination contribute to a doubling of the cost of injectable medication. What is needed is a disposable syringe containing the exact dosage required without the necessity of transfer handling.

However, syringes of a plastic-like nature introduce new problems in the area, i.e. long term storage problems. On storage of a sustained time nature, the medication is liable to be contaminated by plastic leaching. Therefore, the disposable syringes of the art are limited to use immediately subsequent to charging the same with the medication. Thus, we are again encountered by transfer handling, and the logistics which raise the cost of injectable medication.

Glass and stainless steel have a long term acceptable history both as syringes and as a means of storing medication. However, the costs of such syringes are prohibitive prior to this because of the expensive methods of manufacture. One of the expensive steps in manufacture is the fastening of the hypothermic needle to the barrel body of the syringe, and this presents problems itself. One method to reduce cost was to use adhesives. However, adhesives for this purpose introduce a new interface, and is relatively unknown when considering the long term effects on storage of the medication. Some have attempted to bond the needle directly to the glass. However, the temperatures required discolored the stainless steel, it could lose its temper, and the facts of carbon deposits negate this approach.

The process of the present invention answers the needs of the art. The system of fabricating the syringe by this method significantly reduces the cost of a syringe, and it is now possible to have a glass syringe which is disposable, and acceptable as a medication charged unit over a long term period.

The disposable, one unit, single use glass syringe in accordance with the present invention, is useful in replacing present syringes which are now almost manufactured of plastic. These present plastic syringes have been found to have a number of drawbacks including the tendency of the plastic materials to contaminate the medicine as a result of plastic leaching. This problem is eliminated by the use of applicant's glass material and contamination free unit dose syringes are produced using contamination free glass and steel as well as a certain amount of silicone rubber in the plunger sealing portions.

The syringe structure and its method of manufacture, in accordance with the present invention, require only a limited number of relatively simple manufacturing or assembly steps which are readily performed on automatic glass manufacturing machinery. This results in the provision of a disposable syringe which has the advantage of overcoming in-situ storage contamination of the medication at a modest manufacturing cost. The syringe structure and method of assembly also are adapted to convenient coding or identification through the use of colored plastic gripping sleeves which are readily applied during the syringe manufacturing steps.

The improved glass syringe in accordance with the present invention comprises a generally tubular barrel-like body portion which may be cut from glass tubing of a right circular cylindrical variety and a similar tubular glass bead which is used to mount and to seal a needle into the barrel-like syringe body. Both the bead and the barrel of the syringe body are made from common stock of a right circular hollow cylindrical tube.

Accordingly, an object of the present invention is to provide an improved glass disposable single use, medication charged syringe.

Another object of the present invention is to provide a relatively inexpensive glass disposable syringe in which the medication may be stored prior to use over extended periods of time.

Another object of the present invention is to provide a glass disposable syringe wherein the body portion is assembled with a minimum of steps such as cutting and fusing.

Another object of the present invention is to provide a glass disposable one unit charge syringe adapted for accomodating a variety of amounts of medication including relatively small dosages such as one quarter cc. during manufacture.

Another object of the present invention is to provide a glass disposable, medication charged syringe which is contamination free relative the charged medication even after extended storage.

A further object of the present invention is to provide a glass disposable syringe which is adapted for relatively simple and reliable color coding by a gripping sleeve means.

A still further object is a disposable, single use, charged syringe which eliminates transfer handling common today in hospitals.

A still further object is a syringe which significantly cuts the costs of injectable medication.

Other and further objects of the present invention will become more apparent upon an understanding of the illustrative embodiments about to be described, or will be indicated in the appended claims, and various advantages not referred to herein will occur to one skilled in the art upon employment of the invention in practice.

BRIEF DESCRIPTION OF THE DRAWINGS

A preferred embodiment of the invention has been chosen for purposes of illustration and description and is shown in the accompanying drawings, forming a part of the specification, wherein:

FIG. 1 is a perspective view of a preferred embodiment of the syringe barrel-like body as formed from common stock of glass tubing of a right circular hollow cylindrical nature.

FIG. 2 illustrates the barrel for FIG. 1 undergoing a flaring operation.

FIG. 3 is an exploded perspective view illustrating the needle and the glass mounting bead for attaching the needle to the barrel. As shown, the glass mounting bead is formed of a right circular hollow cylindrical tube of common stock nature.

FIG. 4 is a perspective view illustrating the attaching or sealing of the steel needle within the glass bead or tube by means of insertion and the application of heat.

FIG. 5 is a perspective view illustrating the insertable attachment of the bead and needle assembly to the syringe barrel-like body by the application of heat.

FIG. 6 illustrates a plastic flared gripping sleeve applied to the assembled syringe body portion which can also be used for identification of the medication charge through color.

FIG. 7 is a vertical sectional view of the syringe taken along line 7—7 on FIG. 6 showing the application of a complementary plunger after the charging of the syringe with medication.

DESCRIPTION OF THE PREFERRED EMBODIMENT

The preferred embodiment of the disposable, single use, one unit, glass syringe body 1 in accordance with the present invention comprises three members which are the tubular glass barrel-like body 2, illustrated in FIG. 1, on which the stainless steel needle 3 is mounted using the tubular glass needle bead 4. The assembly of the syringe body is performed in a number of relatively simple steps on automatic machinery in the manner illustrated in FIGS. 1 through 5.

In this embodiment, disposable dose syringe comprises the combination of a hollow glass tubular barrel with walls of uniform thickness and being of circular cross section at its outer and inner surfaces, said barrel having one outwardly flared end and having the other end comprising a hollow right circular cylinder, a steel needle mounted on said other end of said barrel, the mounting for said needle comprising a glass hollow right circular cylinder whose outer cylindrical glass surface is welded to the complementary inner cylindrical glass surface of said other end of said barrel, and said steel needle passing through and being sealed to the hollow center of said glass bead.

The first automatic manufacturing step comprises the flaring of the upper end of the blass barrel 2 by the usual flaring method including a heating of the top of the barrel 2, by suitable flames and by a mechanical shaping or formation of the flared portion using a flaring tool 5 on the rotating barrel 2. The barrel-like body is initially formed by cutting a right circular hollow glass cylindrical tube from common stock.

The syringe needle 3, which may be stainless steel is attached to the glass barrel 2 through the intermediation of a needle mounting bead 4 as illustrated in FIG. 3. The bead is initially cut from a right circular hollow glass cylindrical tube of common stock. FIG. 4 shows the glass tube 4 being sealed or fused to the steel needle 3 by a heating step wherein the tube 4 and the needle 3 are rotated at a pair of heating flames 6 to form a bead. At the conclusion of the bead sealing step, as illustrated in FIG. 4, the glass bead has been sealed to the steel needle 3.

The assembly consisting of the needle 3 and the bead 4 is then inserted within the lower end of the flared syringe barrel or tube 2. As illustrated in FIG. 5, the rotating barrel or tube 2 and needle assembly 3, 4, are heated to cause the formed bead 4 to be welded or fused to the adjacent inner surface 7 of the syringe barrel or tube 2. At the completion of this operation, a glass dose syringe body 1 has been provided formed from the three syringe elements, namely the barrel 2, the bead 4, and the needle 3. The flared form of the syringe barrel 2 is useful in facilitating a color coding means for the syringe. This coding means comprises a molded or otherwise formed colored plastic gripping sleeve 8 having a mating form to the flared end of the barrel-like body. This is slipped upwardly and into the indicating position at the flared portion of the syringe barrel 2.

After the completion of the above described syringe body 1 assembly steps, the syringe is completed by being annealed, sterilized, and filled with the desired medicine or dosage. Once the exact dosage has been placed in the assembled syringe body with the lower end of the needle capped, a plunger with a sealing silicone portion is placed in position within the syringe barrel 2 thereby completing a disposable, single use, medication charged syringe.

It will be seen that an improved three piece syringe body has been described together with a preferred and simplified method of assembling the syringe body. The syringe takes advantage of the excellent storage characteristics of glass permitting the disposable syringes to be filled with medication and stored for extended periods without dose contamination. The result is an improved, simplified, medication charged syringe adapted for extended storage periods and for containing exact dosages including relatively small dosages. The syringe is adapted for assembly upon automatic machines.

As various changes may be made in the form, construction and arrangement of the invention and without departing from the spirit and scope of the invention, and without sacrificing any of its advantages, it is to be understood that all matter herein is to be interpreted as illustrative and not in a limiting sense.

I claim:

1. A disposable single use syringe glass body adapted to receive a complementary plunger having a one unit charge therebetween fabricated by the process comprising:

insertably fusing in first sequence a hollow hypodermic needle into a first right circular cylindrical hollow glass tube, insertably fusing in second sequence said first tube into a second right circular hollow cylindrical glass tube having walls of uniform thickness and a flared end of open construction adapted to receive in sequence said charge and said plunger.

2. The disposable single use syringe body of claim 1 wherein said second hollow tube is initially subject to flaring.

3. The disposable single use syringe body of claim 1 wherein in first sequence said hypodermic needle is inserted into said first tube end and fused by rotating the tube between a pair of heating flames.

4. The disposable single use syringe body of claim 1 wherein said first tube in second sequence is inserted into said second tube and rotated between a pair of heating flames to weld said first tube to said second tube.

5. The disposable single use syringe body of claim 1 wherein said second tube is insertably mounted into a colored gripping means having a mating form to said flared end of said second tube.

6. A process of making a disposable single use syringe body adapted to receive a complementary plunger having a one unit charge therebetween comprising:
   insertably fusing in first sequence a hollow hypodermic needle into a first right circular cylindrical hollow glass tube,
   insertably fusing in second sequence said first tube into a second right circular hollow cylindrical glass tube having walls of uniform thickness and a flared end of open construction adapted to receive in sequence said charge and said plunger.

7. The process of claim 6 wherein said second hollow tube is initially subject to flaring.

8. The process of claim 6 wherein in first sequence said hypodermic needle is inserted into said first tube and fused by rotating the tube between a pair of heating flames.

9. The process of claim 6 wherein said first tube in second sequence is inserted into said second tube and rotated between a pair of heating flames to weld said first tube to said second tube.

10. The process of claim 6 wherein said second tube is insertably mounted into a colored gripping means having a mating form to said flared end of said second tube.

11. The process of claim 6 wherein said disposable glass body is charged with medication and fitted with a plunger.

* * * * *